United States Patent
Vogler et al.

(10) Patent No.: US 10,463,538 B2
(45) Date of Patent: Nov. 5, 2019

(54) LASER DEVICE FOR MATERIAL PROCESSING

(71) Applicant: Wavelight GmbH, Erlangen (DE)

(72) Inventors: Klaus Vogler, Blankenhain (DE); Olaf Kittelmann, Berlin (DE); Edlef Buettner, Berlin (DE); Jan Popien, Berlin (DE)

(73) Assignee: Wavelight GmbH (DE)

( * ) Notice: Subject to any disclaimer, the term of this patent is extended or adjusted under 35 U.S.C. 154(b) by 0 days.

(21) Appl. No.: 15/911,903

(22) Filed: Mar. 5, 2018

(65) Prior Publication Data

US 2018/0256391 A1    Sep. 13, 2018

(30) Foreign Application Priority Data

Mar. 13, 2017   (DE) .................. 10 2017 002 434

(51) Int. Cl.
| | |
|---|---|
| *A61F 9/008* | (2006.01) |
| *H01S 3/00* | (2006.01) |
| *B23K 26/70* | (2014.01) |
| *A61N 5/067* | (2006.01) |
| *B23K 103/00* | (2006.01) |

(52) U.S. Cl.
CPC ............ *A61F 9/008* (2013.01); *A61F 9/0084* (2013.01); *A61F 9/00825* (2013.01); *B23K 26/705* (2015.10); *H01S 3/005* (2013.01); *A61F 2009/00844* (2013.01); *A61F 2009/00872* (2013.01); *A61N 2005/067* (2013.01); *B23K 2103/32* (2018.08)

(58) Field of Classification Search
CPC ...... A61F 9/008; A61F 9/009; A61F 9/00825; A61F 9/00804; A61F 2009/00872; G01T 1/24; A61N 2005/067; H01S 3/005
USPC ................ 356/121–127; 128/898; 606/2–19; 607/88–94
See application file for complete search history.

(56) References Cited

U.S. PATENT DOCUMENTS

| | | | |
|---|---|---|---|
| 6,666,855 B2 * | 12/2003 | Somani | A61F 9/008 250/252.1 |
| 9,755,383 B2 * | 9/2017 | Seok | H01R 24/66 |
| 2012/0015318 A1 * | 1/2012 | Kasenbacher | A61C 1/0046 433/29 |

(Continued)

FOREIGN PATENT DOCUMENTS

| | | | |
|---|---|---|---|
| CA | 2774879 | * | 5/2011 |
| WO | 2011/060797 A1 | | 5/2011 |
| WO | 2015/176773 A1 | | 11/2015 |

*Primary Examiner* — Hoa Q Pham
(74) *Attorney, Agent, or Firm* — Keiko Ichiye, Esq.

(57) ABSTRACT

In certain embodiments, a laser device for laser processing of an eye comprises a source of a pulsed laser beam, a detector system that photodetects partial beams generated from the laser beam, and a control unit that evaluates the detection signals. A first detection element of the detector system provides a first detection signal based on single-photon absorption. A second detection element provides a second detection signal based on two-photon absorption. The control unit puts the measured signal strengths of the two detection signals into a ratio to one another. Variations in the resulting ratio value may be traced back to variations in the pulse duration and/or wave front of the laser beam. The control unit may initiate countermeasures to maintain the beam quality of the laser beam.

8 Claims, 1 Drawing Sheet

(56) References Cited

U.S. PATENT DOCUMENTS

2014/0228825 A1  8/2014 Gorschboth et al.
2014/0361145 A1  12/2014 Vogler et al.
2015/0335478 A1  11/2015 Cherkas et al.

* cited by examiner

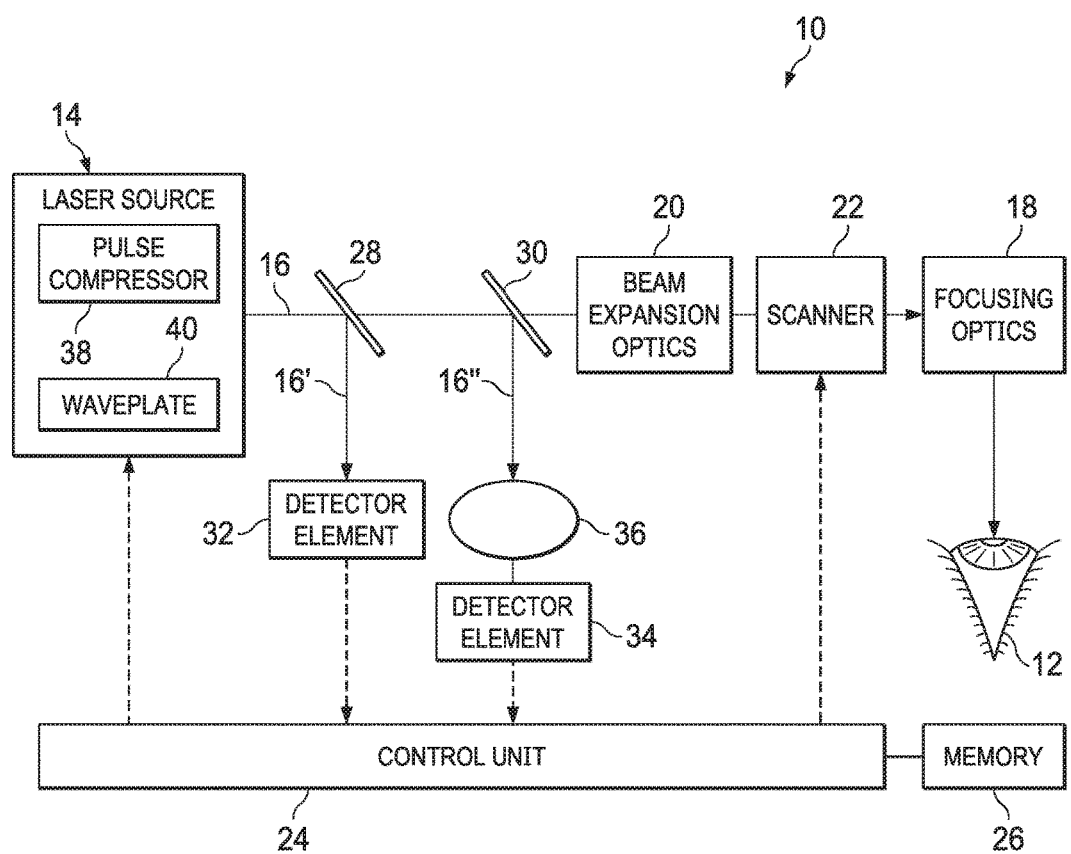

LASER DEVICE FOR MATERIAL PROCESSING

CROSS REFERENCE TO RELATED APPLICATIONS

This application claims priority to German Patent Application Serial Number 10 2017 002 434.0, filed 13 March, titled "LASER DEVICE FOR MATERIAL PROCESSING," which is hereby incorporated by reference in its entirety.

FIELD

The present disclosure relates to a laser device for material processing.

BACKGROUND

The importance of ultrashort pulse lasers for processing a wide range of materials is increasing more and more. In particular, ultrashort pulse laser radiation can be used to produce cuts in transparent materials (transparent for the radiation wavelength) deep in the material, i.e. below the surface. In the case of the short pulse durations in question here in the range of pico-femto- or attoseconds, the non-linear interaction processes between laser radiation and material that are responsible for the material separation (disruption) are concentrated mainly on the region of the beam focus, so that a high cutting accuracy can be achieved with a limited zone of undesirable collateral damage at the same time. In medical applications in particular, e.g. in laser-based eye surgery, the comparatively low energy density accompanying the ultrashort pulse durations that is required to achieve the desired interaction between radiation and tissue is a great advantage.

Ultrashort pulse lasers, especially those delivered as "turnkey" systems to customers by a laser manufacturer, are systems with a high degree of complexity, which usually require constant monitoring and adjustment of the pulse parameters to maintain the efficacy of the material processing at a desired level. In laser applications using ultrashort pulse radiation, the interaction between the radiation and the material is based primarily on non-linear processes, which call for a certain intensity and energy density. This can be achieved by strong focusing of the radiation pulses with the result that in the material to be processed, a very high peak intensity (e.g. more than 10 TW/cm$^2$) and energy density (e.g. more than 500 J/cm$^3$) can occur in an extremely small volume.

As soon as an optimal set of pulse parameters has been determined for a specific material to be processed, it is often necessary for uniform processing to maintain the pulse properties in a certain range (not too low and not too high), in order to keep the desired primary interaction effects and any undesirable, possibly harmful secondary effects in balance. Two approaches can generally be distinguished when monitoring the beam quality of a laser beam: the sequential method and the simultaneous method. In the sequential method, the test is carried out timewise before the actual material processing in a separate upstream test step, in which e.g. sample pieces are processed by way of testing or certain beam parameters are measured directly at the location of the beam focus. In the simultaneous method, on the other hand, the beam test takes place during the actual material processing. The two methods can be described as an offline method (sequential) and an inline method (simultaneous). In material processing using ultrashort pulse laser radiation, a peak intensity that is stable from pulse to pulse in the target region is a key parameter for reliable and effective processing. In applications of this kind, inline monitoring of the peak intensity is therefore desirable.

An inline method for monitoring the quality of a laser beam is known from WO 2011/060707 A1. In this, a portion of the laser beam used for the material processing is coupled out and focused on a non-linear crystal, in which the second harmonic of the basic wavelength of the laser beam is produced by non-resonant frequency mixing. The conversion efficiency of the frequency doubling is in a direct ratio to the peak intensity of the laser pulses applied to the crystal and consequently depends on the peak intensity of the pulses of the (main) laser beam. Power changes in the second harmonic can—insofar as other influence factors can be excluded—be traced back accordingly to a change in the beam quality and/or the pulse duration.

SUMMARY OF THE DISCLOSURE

On the other hand, the present disclosure facilitates inline monitoring of a laser beam not by the production of a higher harmonic from the basic wavelength of the laser beam, but by power measurements on the basis of single-photon absorption and two-photon absorption. A laser device for material processing is accordingly provided according to certain embodiments, comprising a source of a pulsed laser beam, a detector system for the photodetection of a plurality of partial beams generated from the laser beam by radiation outcoupling and provision of corresponding detection signals, and an evaluation unit linked to the detector system for evaluation of the detection signals, wherein a first of the detection signals is based on single-photon absorption and a second of the detection signals is based on two-photon absorption. The two-photon absorption is based on the process that a molecule passes from a basic state to an excited state if the molecule absorbs two photons simultaneously. A detector operating on the principle of two-photon absorption has a suitably chosen band gap between the basic state and the excited state, so that for a given wavelength of the laser radiation it only emits a detection signal if two-photon absorption events occur. In contrast to this, in single-photon absorption a single photon is sufficient to cause a transition of a molecule to an excited state.

Averaged over time, the first detection signal (i.e. the detection signal based on single-photon absorption) is proportional to the average power of the laser radiation, which is linked to the average pulse energy via the formula $E_{Puls} = P_{ave}/f_{rep}$, wherein $P_{ave}$ describes the average power, $f_{rep}$ describes the pulse repetition rate and $E_{Puls}$ describes the pulse energy. On the other hand, the second detection signal (which is based on two-photon absorption) when averaged over time is proportional to the product of average power and peak intensity on the detector surface, wherein the peak intensity is proportional for its part to the quotient of average power and the product of pulse repetition rate $f_{rep}$, pulse duration $\tau_{Puls}$ and spot size, thus size of the laser beam on the detector surface, $A_{Spot}$. Thus the following relationship applies to the quotient of second detection signal and first detection signal:

$$S_{Zpd}/S_{Epd} = c^*(P_{ave})/(A_{Spot}*\tau_{Puls}*f_{rep})$$

where $S_{Zpd}$ describes the temporal average value of the second detection signal based on the detection of two-photon absorption events, $S_{Epd}$ describes the temporal average value of the first detection signal based on the detection of single-photon absorption events and c describes a proportionality constant. Since the term $(P_{ave})/(A_{Spot}*\tau_{Puls}*f_{rep})$ is proportional to the peak intensity, a proportionality to the peak intensity of the laser radiation is yielded for the quotient of $S_{Zpd}$ and $S_{Epd}$. Assuming a constant repetition rate $f_{rep}$ and a constant average power $P_{ave}$, changes in the quotient of $S_{Zpd}$ and $S_{Epd}$ can accordingly be traced back to changes in the pulse duration $T_{Puls}$ or/and the spot size $A_{qspot}$, wherein the latter represents a measure of the focusability.

In view of these relationships, it is provided in certain embodiments of the laser device according to the invention that the evaluation unit is configured to put measured values of the first and the second detection signal into a ratio to one another and in particular to divide a measured value of the second detection signal by a measured value of the first detection signal.

In inline monitoring of the beam quality in particular, it is desirable to be able to introduce countermeasures quickly if it is established that the beam quality does not conform to the desired requirements. In certain embodiments it is provided accordingly that the evaluation unit is part of a control unit, which is configured to bring about at least one predetermined reaction depending on the fact that an actual state defined by measured values of the first and the second detection signal deviates in a predetermined manner from a target state.

The predetermined reaction can be an operational shutdown of the source, for example, or/and the output of a message. Alternatively or in addition, the predetermined reaction can comprise a controlling of a component of the laser device influencing the pulse duration of the laser beam, in particular of a controllable pulse compressor, by the control unit. Another possible reaction consists in a controlling of a component of the laser device influencing the wave front of the laser beam, in particular of a controllable waveplate arrangement, by the control unit.

In certain embodiments the laser device further comprises focusing optics for focusing the laser beam on an object to be processed and a focus control device for spatial control of the focus position of a laser beam, wherein the focus control device comprises at least one transverse control element arranged in the beam path of the laser beam between source and focusing optics for the spatial-transverse control of the focus position. An outcoupling point at which radiation is coupled out from the laser beam for at least one of the partial beams is arranged in this case in the beam path of the (main) laser beam between the source and the at least one transverse control element.

According to certain embodiments, beam expansion optics can be arranged in the beam path of the laser beam between the source and the at least one transverse control element. The outcoupling point can be arranged in this case in the beam path of the laser beam between the source and the beam expansion optics.

For a high sensitivity of a detector element of the detector system operating according to the principle of two-photon absorption, the use of a focusing lens for focusing one of the partial beams onto this detector element is recommended.

BRIEF DESCRIPTION OF THE DRAWING

The invention is explained in greater detail below with reference to the single drawing enclosed. This shows schematically a practical example of a laser device for material processing in FIG. 1.

DETAILED DESCRIPTION OF PREFERRED EMBODIMENTS

Preferred embodiments are explained in greater detail below with reference to FIG. 1. This shows a device, generally designated by 10, for laser-aided material processing. In the example shown, the laser device 10 is used for laser processing of a human eye 12 and for producing intracorneal tissue sections there, for example. In principle, however, the present disclosure is not limited to the use of the laser device 10 in laser-aided eye surgery. Instead of this, the laser device 10 can also be used in particular for cutting laser processing of other biological tissue as well as of non-biological material.

The laser device 10 comprises a laser source 14, which produces a pulsed laser beam 16 with pulse durations in the pico-, femto- or attosecond range. The laser device 10 also comprises focusing optics 18, which are formed by an F-Theta lens, for example. The focusing optics 18 focus the laser beam 16 onto the object to be processed, here the eye 12. Also arranged in the beam path between the laser source 14 and the focusing optics 18 are beam expansion optics (beam expander) 20 and a scanner 22. The beam expansion optics 20 cause an expansion of the beam cross section of the laser beam 16, for example by means of a lens arrangement in the manner of a Galileo telescope. The scanner 22 is used for the transverse and longitudinal control of the focus position of the laser beam 16. For the transverse deflection the scanner 22 can comprise a galvanometrically controlled pair of tilt mirrors or an electrically controlled deflection crystal, for example. For the longitudinal focus control, the scanner 22 can comprise, for example, an optical element influencing the divergence of the laser beam 16, for instance a lens that is longitudinally movable in the beam propagation direction or a liquid lens of variable refractive power or a deformable mirror. Even if the scanner 22 in FIG. 1 is represented as a single function block, it should be understood that the components of the scanner 22 responsible for the transverse focus control and the longitudinal focus control of the laser beam 16 can be arranged at different points along the beam path of the laser beam 16. For example, a longitudinal control element of the scanner 22 can be formed by a lens, which is contained in the beam expansion optics 20, while one or more transverse control elements (e.g. scanner mirrors) can be arranged in the beam path after the beam expansion optics 20. The scanner 22 can accordingly be formed by a distributed arrangement of various scan components.

To control the laser source 14 and the scanner 22, a processor-aided control unit 24 is provided, which operates according to a control program stored in a memory 26. The control program contains suitable control parameters (for example, in the form of coordinates for the individual firing positions of the laser pulse), which determine the cut geometry to be produced.

To produce fine and precise cuts by means of the laser beam 16, a high spatial and temporal beam quality of the same is desirable. For real-time monitoring of the beam quality of the laser beam 16 (inline monitoring), the laser device 10 has means for producing two partial beams 16', 16" from the laser beam 16. For this purpose the laser device 10 comprises means for coupling out a portion of the radiation of the laser beam 16. These means are arranged in the beam propagation direction ahead of the components of the scanner 22 responsible for the transverse focus control and in the example shown also ahead of the beam expansion optics 20 and comprise, in the practical example in FIG. 1, two semipermeable splitter mirrors 28, 30 arranged behind one another in the beam path of the laser beam 16. Each of the splitter mirrors 28, 30 couples out one of the partial beams 16', 16" respectively from the laser beam 16. In a modified embodiment, only a single partial beam is coupled out from the laser 16 initially, which is then split into the two partial beams 16', 16".

Arranged in the propagation path of the first partial beam 16' is a first detector element 32 and arranged in the propagation path of the second partial beam 16" is a second detector element 34. The detector element 32 operates according to the principle of single-photon absorption, while the detector element 34 operates according to the principle of two-photon absorption. The detection signal emitted by the first detector element 32 is a measure of the average power of the partial beam 16' calculated as a product of the pulse repetition rate and the pulse energy of the radiation pulses of the partial beam 16' and is accordingly also proportional to the average power of the (main) laser beam 16. The detection signal supplied by the second detection element 34, on the other hand, is a measure for the product of average power and peak intensity of the second partial beam 16" and accordingly also a measure for the corresponding product of the (main) laser beam 16. To increase the probability of two-photon absorption events, a short focal length focusing lens 36 (e.g. focal length≈20 mm), for example, is arranged in the beam path of the second partial beam 16" ahead of the detection element 34, which lens focuses the partial beam 16" onto the detection surface of the detection element 34. No special explanation is required that the focusing lens 36 can be formed by a lens group instead of a single lens.

The detection signals of the two detection elements 32, 34 are brought together and evaluated in the control unit 24. In particular, the control unit 24 calculates a quotient of the detection signals of the two detection elements 32, 34 according to the following mathematical relationship:

$$S_{Zpd}/S_{Epd}=c*(P_{ave})/(A_{Spot}*\tau_{Puls}*f_{rep})$$

where $S_{Zpd}$ describes the temporally averaged value of the detection signal supplied by the detection element 34, $S_{Epd}$ describes the temporally averaged value of the detection signal supplied by the detection element 32, $P_{ave}$ describes the average radiation power of the laser beam 16, $A_{Spot}$ describes the spot size of the partial beam 16" on the detection surface of the detection element 34, $T_{Puls}$ describes the pulse duration, $f_{rep}$ describes the pulse repetition rate and c describes a proportionality constant. Assuming a constant pulse repetition rate $f_{rep}$ and a constant average power $P_{ave}$, variations in the ratio $S_{Zpd}/S_{Epd}$ can therefore be traced back to variations in the pulse duration $\tau_{Puls}$ or/and the spot size $A_{Spot}$.

The above ratio of $S_{Zpd}$ to $S_{Epd}$ is calculated by the control unit 24 at least once and preferably repeatedly, for example at regular intervals in time or substantially continuously, during an emission of the laser beam 16. Such an emission takes place as part of the actual processing procedure in which the eye 12 is processed with the laser beam 16. An emission of the laser beam 16 can also take place in a temporally preceding test procedure, in which the laser device 10 is put into operation for test purposes. The actual state of the laser device 10 represented by the quotient of $S_{Zpd}$ and $S_{Epd}$ is compared by the control unit 24 with a target state. As soon as the control unit 24 establishes that the actual state differs in a certain manner from the target state, it initiates a predetermined reaction. This reaction can comprise, for example, a shutdown of the laser source 14, so that the emission of the laser beam 16 is interrupted. Alternatively or in addition, the reaction can comprise an output of an optical and/or acoustic message. The message can be displayed, for example, in text or graphic form on a monitor or it can involve a signal lamp. An acoustic alert is also conceivable as part of the message. Instead of an operating interruption of the laser source 14, it is conceivable that the control unit 24 initiates a suitable correction measure, by means of which the actual state can again be approximated more closely to the target state in the context of a control loop. A possible correction measure consists in the controlling (by the control unit 24) of a suitable controllable component, by means of which the pulse duration of the radiation pulses of the laser beam 16 can be influenced. Such a component is a pulse compressor 38, for example, which can be contained in the laser source 14 as part of an amplifier downstream of a laser resonator. To produce high pulse intensities amplifiers are often used, which operate according to the principle of Chirped Pulse Amplification. In this case the pulses generated by the resonator are first spatially stretched before being compressed again after passing through an amplifier medium. By suitable control of a pulse compressor used for this compression, the control unit 24 can attempt accordingly to reduce discrepancies between the measured value of the ratio of $S_{Zpd}$ and $S_{Epd}$ and a desired target value or target range.

Another possible correction measure that can be used alternatively or in addition to the explained influencing of the pulse duration consists in the controlling (by the control unit 24) of a suitable component for influencing the wave front of the laser beam 16. This component can be, for example, a waveplate that is insertable into the beam path in the laser source 14 inside or outside the laser resonator or an arrangement of such waveplates. By modifying the wave front of the laser beam 16, the focusability and thus the portion of the detection surface of the detection element 34 (i.e. spot size $A_{Spot}$) that is irradiated by the focused partial beam 16" can be influenced.

The target state is given, for example, by a reference value of the quotient $S_{Zpd}/S_{Epd}$, which can be stored in the memory 26 and monitored in emission operation of the laser device 10 for deviations from a current value of the quotient $S_{Zpd}/S_{Epd}$. If the detection signal of the detection element 34 (two-photon detector) depends quadratically with sufficient accuracy on the average power of the partial beam 16" and accordingly of the laser beam 16, it can be sufficient to store a single reference value for the proportionality factor between $S_{Zpd}$ and $S_{Epd}$ in the memory 26 for a given pulse repetition rate $f_{rep}$. As soon as the current value of the quotient $S_{Zpd}/S_{Epd}$ departs in emission operation of the laser device 10 from a defined tolerance range around the stored reference value, the control unit 24 initiates at least one of the explained reactions. Above all, if the detection signal of the detection element 34 does not display a quadratic dependence on the average laser beam power with the desired accuracy, it is conceivable to include a reference curve across the overall power range of the laser device 10 instead of a single reference value applying to all power values and to store it in the memory 26. This curve specifies an associated reference value for the quotient $S_{Zpd}/S_{Epd}$ respectively for various values of the average radiation power of the laser device 10. The curve can be produced in tabular form, for example, or represented by a mathematical formula (e.g. a Taylor series with at least three powers). In emission operation of the laser device 10, the adherence to the reference curve is monitored on an ongoing basis either on the basis of the stored table (if applicable with interpolation between the value pairs contained in the table) or on the basis of the formula, depending on the form in which the curve is stored in the memory 26. A tolerance range can be determined even when using a reference curve as a representation of the target state, which range can be of equal magnitude over the entire curve or if applicable of different magnitude in the different parts of the curve.

The measured values for the detection signals of the detection elements 32, 34 or/and the calculated values of the quotient $S_{Zpd}/S_{Epd}$ are stored continuously in the memory 26 in certain embodiments of the control unit 24. Alternatively or in addition, they are displayed continuously on a computer monitor (not shown in FIG. 1), so that the operator receives direct information about the beam quality of the laser beam 16 during the laser procedure.

According to a possible further development, at least one of the detection elements 32, 34 can be formed as a position-sensitive detector, the detection signal of which is composed of a plurality of partial signals, on the basis of which the control unit can calculate the position of the relevant partial beam 16' or 16" on the detection surface of the detector. Such sensors, which can register the one- or two-dimensional position of a light point, are generally familiar to experts and a more detailed explanation can thus be dispensed with. By determining the position of the partial beam 16' or 16", the control unit 24 can recognise possible variations in the beam direction of the laser beam 16 and initiate a suitable reaction if the variations detected exceed a certain permissible variation range. In particular, suitable countermeasures are possible as a reaction to reduce the directional variations of the laser beam 16. It is conceivable in this regard that the control unit 24 provides the components of the scanner 22 (e.g. a pair of tilt mirrors) responsible for the transverse position control of the beam focus of the laser beam 16 with correspondingly corrected control values, so that the directional variations of the laser beam 16 observable ahead of the beam expansion optics 20 are reduced or have even largely disappeared after the scanner 22.

Alternatively or additionally to a correction of directional variations of the laser beam 16, the control unit can display detected directional variations in a manner comprehensible to the user of the laser device 10 on a computer monitor and/or archive them in the memory 26.

The invention claimed is:

1. Laser device for material processing, comprising
    a source of a pulsed laser beam;
    a detector comprising a plurality of detector elements configured to:
        photodetect a plurality of partial beams generated from the laser beam by radiation outcoupling; and
        provide corresponding detection signals, a first detector element providing a first detection signal based on single-photon absorption and a second detector element providing a second detection signal based on two-photon absorption; and
    a processor-aided computer linked to the detector system for evaluation of the detection signals, the computer configured to:
        calculate a quotient $S_{Zpd}/S_{Epd}$ of the detection signals of the detector elements, where $S_{Zpd}$ describes a temporally averaged value of the second detection signal of the second detector element, and $S_{Epd}$ describes a temporally averaged value of the first detection signal of the first detector element; and
        in response to a variation in the quotient $S_{Zpd}/S_{Epd}$, trace back to a variation in a spot size of the laser beam on a detection surface of the first detection element.

2. Laser device according to claim 1, wherein the computer is configured to effect at least one predetermined reaction in response to a variation in the quotient $S_{Zpd}/S_{Epd}$.

3. Laser device according to claim 2, wherein the at least one predetermined reaction comprises an operating shutdown of the source or the output of a message.

4. Laser device according to claim 2, wherein the at least one predetermined reaction comprises controlling a component of the laser device influencing the pulse duration of the laser beam.

5. Laser device according to claim 2, wherein the at least one predetermined reaction comprises controlling a component of the laser device influencing the wave front of the laser beam.

6. Laser device according to claim 1, further comprising:
    focusing optics for focusing the laser beam onto an object to be processed; and
    a focus control device for the spatial controlling of a focus position of the laser beam, the focus control device comprising at least one transverse control element arranged in the beam path of the laser beam between the source and focusing optics for the spatial-transverse control of the focus position,
    wherein an outcoupling point, at which radiation is coupled out from the laser beam for at least one of the partial beams, is arranged in the beam path of the laser beam between the source and the at least one transverse control element.

7. Laser device according to claim 6, further comprising:
    beam expansion optics arranged in the beam path of the laser beam between the source and the at least one transverse control element, wherein the outcoupling point is arranged in the beam path of the laser beam between the source and the beam expansion optics.

8. Laser device according to claim 1, further comprising:
    a focusing lens for focusing one of the partial beams onto a detector element of the detector system that acts according to the principle of two-photon absorption.

* * * * *